United States Patent [19]

Horisberger et al.

[11] 4,081,330

[45] Mar. 28, 1978

[54] PRODUCTION OF A MILKCURDLING ENZYME

[75] Inventors: Marc Horisberger, Mt-Pelerin; Tomaso Sozzi, Lausanne; Robert Pousaz, Arnex-sur-Orbe, all of Switzerland

[73] Assignee: Societe d'Assistance Technique pour Produits Nestle, S.A., La Tour-de-Peilz, Switzerland

[21] Appl. No.: 698,534

[22] Filed: Jun. 22, 1976

Related U.S. Application Data

[63] Continuation of Ser. No. 529,029, Dec. 3, 1974, abandoned.

[30] Foreign Application Priority Data

Dec. 19, 1974 Switzerland ............. 17760/74

[51] Int. Cl.$^2$ ............................................. C07G 7/02
[52] U.S. Cl. ................................... 195/66 R; 195/62; 426/36; 426/63
[58] Field of Search ............... 195/66 R, 62; 426/36, 426/61, 63

[56] References Cited

U.S. PATENT DOCUMENTS 2,337,947 12/1943 Thornley et al. ............. 195/66 R

OTHER PUBLICATIONS

Babel, et al., Action in Cheese Ripening of an Enzyme Preparation from Chicken Proventriculi, Including Manufacture of a New Type Cheese, J. Da. Sci., vo. 26 1943 (pp. 331-336).
Davis, J. G., Cheese, vol. I, American Elseiier Pub. Co., Inc. N.Y. 1965 (pp. 244-251).

Primary Examiner—David M. Naff
Attorney, Agent, or Firm—Kenyon & Kenyon, Reilly, Carr & Chapin

[57] ABSTRACT

A rennet-like milk-curdling enzyme is obtained from the stomach tissue of poultry by immersing the tissue in an aqueous saline solution with a pH-value below 4, and thereafter separating out undissolved materials to leave a solution containing the enzyme.

12 Claims, 1 Drawing Figure

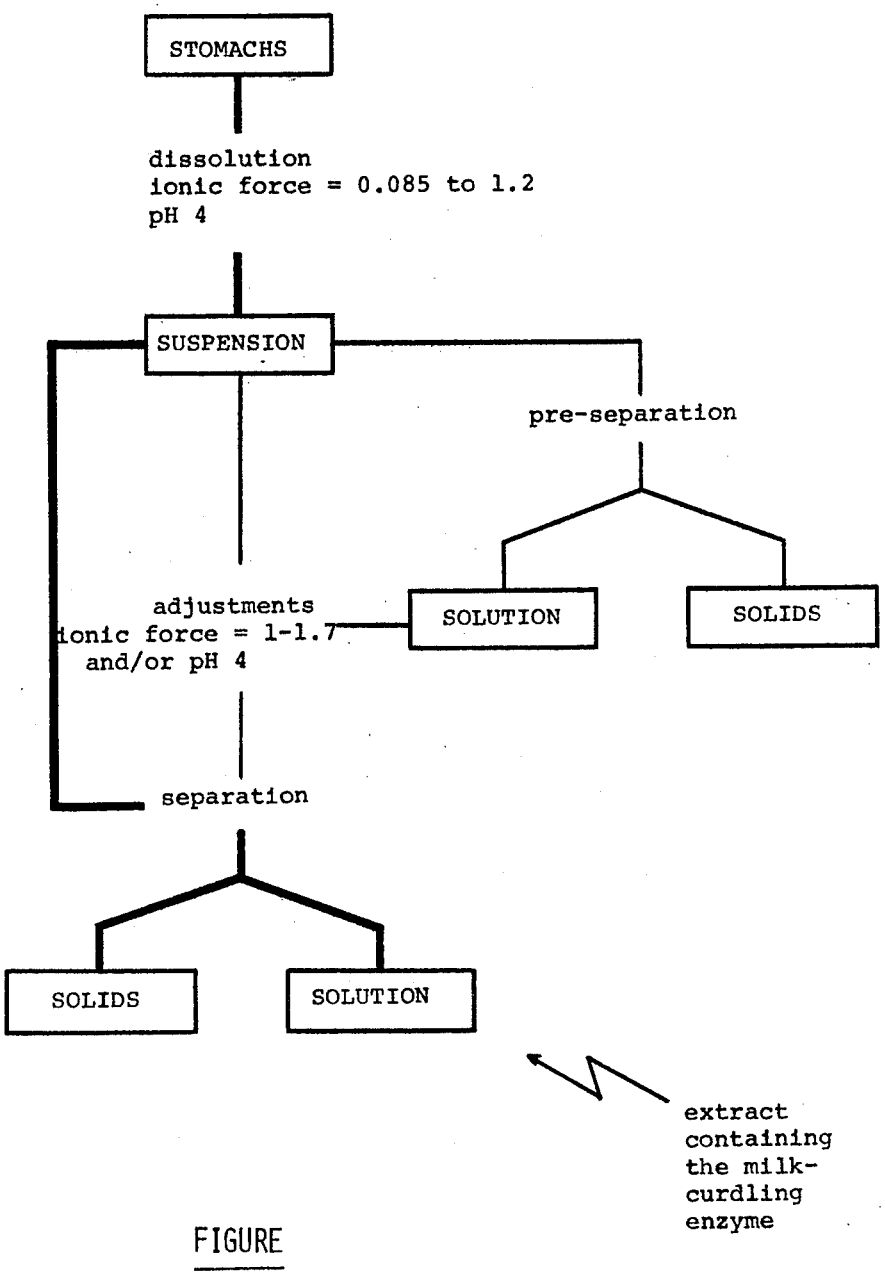
FIGURE

PRODUCTION OF A MILKCURDLING ENZYME

This is a continuation of application Ser. No. 529,029 filed Dec. 3, 1974, now abandoned.

This invention relates to the production of enzymatically active products. More particularly, the invention relates to the production, from the stomachs of poultry, of products which coagulate milk and which have the characteristics of rennet.

Rennet, a product of natural origin with a coagulating effect on milk casein, is an extract obtained from the gastric mucosa of calves fed exclusively on milk. This coagulating effect is due to the presence in this extract of an enzyme, known as rennin, which has a specific proteolytic activity with respect to K-casein. In view of the nature of its source, rennet can only be obtained irregularly in quantities which vary according to season and which are inadequate for coping with the increasing demand of the dairy and cheese-making industries.

It is for this reason that efforts have been made and are still being made to produce so-called "microbial" rennets, i.e. rennets produced by biosynthesis. Unfortunately, rennets of this kind have the disadvantage of frequently giving rise to the development of unpleasant tastes and/or of forming curds of inadequate quality, especially so far as the production of cheese is concerned.

It is also known that the gastric system of certain birds, especially carnivorous birds, is the centre of intense proteolytic activity of the pepsic type. Israeli Pat. No. 30,520 describes a process for extracting a milk-curdling enzyme by means of an alkaline agent or even by pressing stomachs.

The present invention relates to a process for the production of a milk-curdling enzyme whose activity is greater than that of the pepsin obtained from poultry by alkaline extraction. The process according to the invention is distinguished by the fact that stomach tissue of poultry is treated with an aqueous saline solution with a pH-value of less than 4, the undissolved materials are separated and the solution containing the milk-curdling enzyme is subsequently recovered.

Although generally speaking the stomachs of poultry, especially domestic poultry, yield a milk-curdling enzyme of suitable quality, it is preferred to use, as stomach tissue, glandular or proventricular stomach tissue, because it is in these organs that the maximum concentration of pepsinogen, the precursor of pepsin, is found.

The treatment of these tissues comprises immersing them in an aqueous saline solution with a pH value of below 4 which may be adjusted by means of a buffer solution or any acidification agent in the form of a mineral or organic, preferably food-grade acid, such as hydrochloric acid for example. The tissue/solution contact surface should with advantage be as large as possible in view of the fact that wettability is essential. In addition, the tissue/solution suspension is preferably vigorously stirred. The best extraction yields of active product are obtained with saline solutions having approximate ionic force values of from 0.085 to 1.2, disregarding the acidification agent, for example solutions of sodium chloride with concentrations of from 0.5 to 7%. The salt used is preferably sodium chloride, essentially in view of the "food-grade" application of the milk-curdling enzyme, although it is obvious that any other salt (potassium chloride, sodium phosphate or sulphate, etc.) or mixture of salts giving a suitable ionic force may also be used. The optimum contact time, i.e. the time beyond which the extraction yield does not increase any further, or even decreases, is of the order of 15 to 20 minutes for possible working temperatures in the range from 0° C to 40° C. Finally, the milk-curdling enzyme is recovered from the solution obtained following separation of the solid and liquid phases which may be carried out by any suitable method, such as filtration, but which, in view of the nature of the suspension, may be carried out in a highly practical manner by centrifuging.

The various stages of the process according to the invention are shown in thick lines in the accompanying drawing in which optional and preferred modifications are also shown, but in thin lines.

In a first modification, the ionic force value of the liquid phase of the suspension is re-adjusted or modified before phase separation, because it is preferred to carry out this separation at values which enable a large quantity of the uninteresting protein fractions extracted by the acid treatment to be precipitated without, at the same time, introducing too much salt into the liquid phase and, hence, interfering with the subsequent reductions in volume. For example if sodium chloride is used as the salt, the concentration of that salt is kept within a range from approximately 6 to 10%. At the same time, the pH-value of the suspension may be re-adjusted to a value below 4, for example to the initial value, because it has been found that the pH-value varies during the treatment.

In a second, preferred modification, which is an improvement in the first modification, the phases of the suspension are separated, for example by centrifuging, the ionic force and/or pH changes taking place in the solution freed from insoluble materials, for example the supernatant phase.

The solution obtained after separation or, preferably, after preseparation and separation, is an extract which contains the milk-curdling enzyme. This extract is in the form of a clouded liquid which may be directly used for coagulating milk. Nevertheless, it is normally preferred to clarify the liquid, in other words to remove fats and oils from it. In addition, in one advantageous embodiment, the pH-value of the optionally clarified extract is reduced to a value around 2, which is the pH-value at which the milk-curdling enzyme develops its greatest activity. This pH-value on the one hand and the presence of salt in a significant concentration on the other hand provide this enzyme in solution with excellent keeping qualities. It is of course possible to concentrate this solution by any means which do not denature the enzyme, for example by evaporation in vacuo or by inverse osmosis. It is also possible to eliminate all the water and to recover the product in dry form, for example by lyophilisation.

In one particular embodiment, a paste of glandular stomachs of chicken is prepared and suspended with vigorous stirring in a 0.88% solution of sodium chloride in deionised water (physiological serum). The pH-value is then adjusted to pH 3 by the addition of hydrochloric acid. After 15 minutes of turbulent contact at ambient temperature, the phases are separated by centrifuging, the supernatant phase is recovered (preseparation), 7% of sodium chloride are added to it and the pH-value re-adjusted to 3 by the addition of more hydrochloric acid. After recentrifuging, the supernatant liquid is freed from fats in a centrifugal separator. Hydrochloric acid is then added to the fat-extracted supernatant phase to adjust its pH-value to pH 2. If desired, the volume is reduced to approximately one third by evaporation in vacuo. The solution, or the concentrated solution, is directly used for curdling milk.

By comparison with the milk-curdling enzyme extracted in alkaline medium, the milk-curdling enzyme extracted in accordance with the invention in acid medium shows almost twice the activity for the same volume, which is reflected in a better extraction yield in acid medium. In addition, the effects which it produces in milk are similar to the effects produced by calf rennet. For example, cheese produced with this milk-curdling enzyme is barely distinguishable, if at all, from traditional cheese. Accordingly, it complies ideally with the requirements of the dairy and cheese-making industries and constitutes so to speak a "poultry rennet".

The process according to the invention is illustrated by the following Examples.

EXAMPLE 1

56 kg of the glandular stomachs of chickens are ground in a Stephan mill fitted with a screen having holes 1.5 mm in diameter, and the product of grinding immersed in 165 liters of deionised water containing 1.45 kg of NaCl. A 12.5% solution of HCl is then added until a pH value of 3 is obtained. The suspension is then vigorously stirred for 15 minutes and subsequently centrifuged at 2000 rpm. in a Heine centrifuge, yielding 55 kg of sediment, which is discarded, and 167.6 kg of supernatant phase to which 11.7 kg of sodium chloride are added, followed by the introduction of 400 g of 12.5% HCl to adjust the pH-value to 2.95. After recentrifuging at 5000 rpm. in a de Laval centrifuge, the supernatant phase is freed from fats by treatment at 28° C in a de Laval centrifugal separator rotating at 7000 rpm. 131.5 kg of solution are obtained in this way. 60 kg of this solution are removed and acidified to pH 2 by the addition of 500 g of 12.5% HCl. The dosages of this acidified solution containing the milk-curdling enzyme produced the following results (acid extraction). The results obtained with a solution acidified to pH 2, obtained by the Israeli process of alkaline extraction referred to at the beginning of this description (alkaline extraction) under otherwise exactly the same conditions, are also given by way of comparison:

|  | acid extraction | alkaline extraction |
|---|---|---|
| % dry matter | 9.90 | 7.15 |
| % fat | 0.04 | 0.01 |
| % calcium | 0.005 | 0.05 |
| % sodium chloride | 7.95 | 6.10 |
| % nitrogen (total) | 0.30 | 0.17 |
| % nitrogen (soluble) | 0.27 | 0.16 |

The bacteriological results relating to the milk-curdling enzyme obtained by the acid process according to the invention are as follows:

| colliforms | negative |
|---|---|
| total germs | 20/ml |
| total sporulated germs | <10/ml |
| micrococcus | <10/ml |
| staphylococcus | <10/ml |
| yeasts and molds | <10/ml |
| lactic ferments | <10/ml |

EXAMPLE 2

The remaining 71.5 kg of the solution obtained in Example 1 are concentrated after fat extraction by evaporation in vacuo using a bath kept at 42° C down to a weight of 21 kg. The concentrated solution is then adjusted to pH 2 by the addition of 370 g of 12.5% HCl. The results of the dosages are as follows (the solution obtained by the alkaline process has obviously undergone the same concentration treatment):

|  | acid extraction | alkaline extraction |
|---|---|---|
| % dry matter | 31.40 | 29.13 |
| % fat | 0.01 | 0.031 |
| % calcium | 0.017 | 0.011 |
| % sodium chloride | 24.4 | 24.0 |
| % nitrogen (total) | 0.95 | 0.71 |
| % nitrogen (soluble) | 0.75 | 0.66 |

EXAMPLE 3

0.1 ml of the acidified solution containing the milk-curdling enzyme obtained by the process described in Example 1 is added to 100 ml of whole milk pasteurised for 3 minutes at 72° C. The temperature is kept at 37° C. The milk is coagulated after 7.5 minutes which, in round figures, corresponds to a strength of 1 : 5300 as against a strength of 1 : 3200 for the acidified, alkaline extraction solution which takes 12.5 minutes to coagulate the same quantity of milk under the same conditions. The strength is calculated in accordance with the following formula:

$$\text{strength} = 10,000 \times 240/t$$

where $t$ is the time required for 0.1 ml of solution containing the curdling enzyme to coagulate 100 ml of milk at a temperature of 37° C.

EXAMPLE 4

0.1 ml of the concentrated and acidified solution containing the milk-curdling enzyme obtained in Example 2 is added to 100 ml of whole milk pasteurised for 3 minutes at 72° C. The temperature is kept at 37° C. The milk is coagulated after 3 minutes which, in round figures, corresponds to a strength of 1 : 13000 as against a strength of 1 : 8000 for the concentrated and acidified alkaline extraction solution of Example 2 which takes 5 minutes to coagulate the same quantity of milk under the same conditions.

EXAMPLE 5

80 kg of whole milk pasteurised for 5 seconds at 65° C are inoculated with 1% of *S. thermophilus* strains, and the milk thus inoculated is kept at 37° C for 1 hour. The pH-value is then 6.20. This milk is then divided into two equal fractions of 40 kg each. The first fraction is then renneted with 20 ml of the concentrated solution of Example 2, an acidified solution containing the milk-curdling enzyme and having a strength of 1 : 13000, followed by the addition of 10 g of $CaCl_2 \cdot H_2O$. At the same time, the second fraction is renneted with 1.5 g of Hansen's rennet of strength 1 : 150000, again followed by the addition of 10 g of $CaCl_2 \cdot H_2O$. Each of the milks is coagulated after 10 minutes.

Each of the curds thus prepared is then subjected to the operations involved in the conventional production of mozzarella which are well known the the man skilled in the art:

working the curds for 6 minutes
placing in moulds
turnover after 15 minutes
draining for 4 hours at 37° C
extrusion of the paste at 60° C
salting to 1%
storage in a cold room in iced water The mozzarellas obtained in this way are tasted after 24 hours. The mozzarella prepared with the solution containing the milk-curdling enzyme is barely distinguishable from the traditional mozzarella prepared with Hansen's rennet. However, it does have a finer and more unctuous paste.

EXAMPLE 6

Two groups of pizzas are prepared using, among other ingredients, the mozzarellas described in Example 5. After cooking, the two groups of pizzas, one containing the traditional mozzarella and the other containing the mozzarella prepared with the solution containing the milk-curdling enzyme, have the same texture and the same taste.

We claim:

1. A process for the production of a milk-curdling enzyme comprising the steps of
    treating stomach tissue obtained from poultry with an aqueous saline solution with a pH-value below 4 and an ionic force of from about 0.085 to 1.2 for a contact time of about 15 to 20 minutes;
    thereafter separating out undissolved material;
    readjusting the pH-value of the remaining solution to a value below 4 and/or readjusting the ionic force of the remaining solution to value of from about 1 to 1.7;
    thereafter separating out any undissolved materials; and
    then recovering the remaining solution containing the milk-curdling enzyme.

2. A process as claimed in claim 1 wherein the aqueous saline solution is a solution of sodium chloride with a concentration of from about 0.5 to 7%.

3. A process as claimed in claim 1 wherein before separation of the undissolved materials, the sodium chloride concentration of the solution is adjusted to values of from about 6 to 10%.

4. A process as claimed in claim 1 wherein the solid materials are separated before adjustment of the ionic force and/or re-adjustment of the pH value.

5. A process as claimed in claim 1 wherein fats are removed from the solution containing the milk-curdling enzyme.

6. A process as claimed in claim 1 wherein the solution containing the milk-curdling enzyme is acidified to a pH value of 2.

7. A process as claimed in claim 1 wherein the solution containing the milk-curdling enzyme is concentrated.

8. A process as claimed in claim 1 wherein the solution containing the milk-curdling enzyme is lyophilised.

9. A process for producing a milk-curdling enzyme comprising the steps of
    immersing poultry stomach tissue selected from the group consisting of glandular and proventricular stomach tissue in an aqueous saline solution with a Ph-value below 4 and an ionic force value of from 0.085 to 1.2 for a contact time of about 15 to 20 minutes to obtain a tissue/solution suspension,
    separating out undissolved material from the tissue/solution suspension,
    thereafter re-adjusting the pH-value of the suspension to a value below 4 and/or the ionic force of the supsension to values of from about 1 to 1.7,
    then separating out undissolved material from the suspension, and
    then recovering the remaining solution as a solution containing the milk-curdling enzyme.

10. A process as set forth in claim 9 wherein the step of re-adjusting the pH value to a value below 4 occurs while the concentration of the salt of the solution is kept within a range from approximately 6 to 10% to obtain an extract containing said enzyme.

11. A process as set forth in claim 9 wherein said second step of separating includes centrifuging of said suspension to obtain said liquid phase as a supernatant phase.

12. A process as set forth in claim 9 wherein said steps of separating includes centrifuging of said suspension to obtain a supernatant phase, and wherein the step of re-adjusting the pH-value of said supernatant phase includes adding acid prior to re-centrifuging of the supernatant phase to obtain a fat-extracted supernatant phase for use in curdling milk.

* * * * *

UNITED STATES PATENT AND TRADEMARK OFFICE
CERTIFICATE OF CORRECTION

PATENT NO. : 4,081,330
DATED : March 28, 1978
INVENTOR(S) : Marc Horisberger, Tomaso Sozzi, Robert Pousaz It is certified that error appears in the above-identified patent and that said Letters Patent are hereby corrected as shown below:

Column 4, Example 2 under acid extraction column, line 2, change "0.01" to --0.017--

Column 6, line 20, change "Ph" to --pH--

Column 6, line 23, after "/" delete -- - --

Signed and Sealed this

Eighth Day of August 1978

[SEAL]

Attest:

RUTH C. MASON
*Attesting Officer*

DONALD W. BANNER
*Commissioner of Patents and Trademarks*